United States Patent [19]

Rosen

[11] 4,390,073
[45] Jun. 28, 1983

[54] BLOOD COLLECTION BAG WEIGHING DEVICE

[75] Inventor: Evan W. Rosen, Tucson, Ariz.

[73] Assignee: Engineering & Research Associates, Inc., Tucson, Ariz.

[21] Appl. No.: 319,573

[22] Filed: Nov. 9, 1981

Related U.S. Application Data

[63] Continuation of Ser. No. 81,164, Oct. 2, 1979, abandoned.

[51] Int. Cl.³ .............................................. G01G 13/02
[52] U.S. Cl. ....................................... 177/118; 177/68; 177/79; 177/DIG. 5
[58] Field of Search .................... 177/116, 118, 45, 48, 177/68, 79, DIG. 5, 229; 340/384 E, 666, 692; 335/174, 230; 361/144, 156

[56] References Cited

U.S. PATENT DOCUMENTS

| | | | |
|---|---|---|---|
| 3,115,152 | 12/1963 | Goldberg et al. | 177/245 X |
| 3,287,721 | 11/1966 | Baehr | 177/245 X |
| 3,671,893 | 6/1972 | Edgar | 335/229 X |
| 3,698,494 | 10/1972 | Gaudin | 177/245 X |
| 3,924,700 | 12/1975 | Lindsey et al. | 177/118 |
| 3,960,224 | 6/1976 | Silvers | 177/47 |
| 4,027,735 | 6/1977 | Floyd | 177/229 X |

Primary Examiner—George H. Miller, Jr.
Attorney, Agent, or Firm—Cahill, Sutton & Thomas

[57] ABSTRACT

A blood collection bag is suspended from a leaf spring, which leaf spring, on being repositioned a specified distance by the weight of a properly filled blood collection bag, energizes an electrical circuit. The electrical circuit generates a pulse to momentarily energize a coil in proximity to a permanent magnet and momentarily disrupt the magnetic field of the magnet. A clamp for terminating the flow of blood to the blood collection bag is actuated on release of a weight retained by the magnetic field of the magnet, which release is achieved by the disruption of the magnetic field on energization of the coil.

8 Claims, 6 Drawing Figures

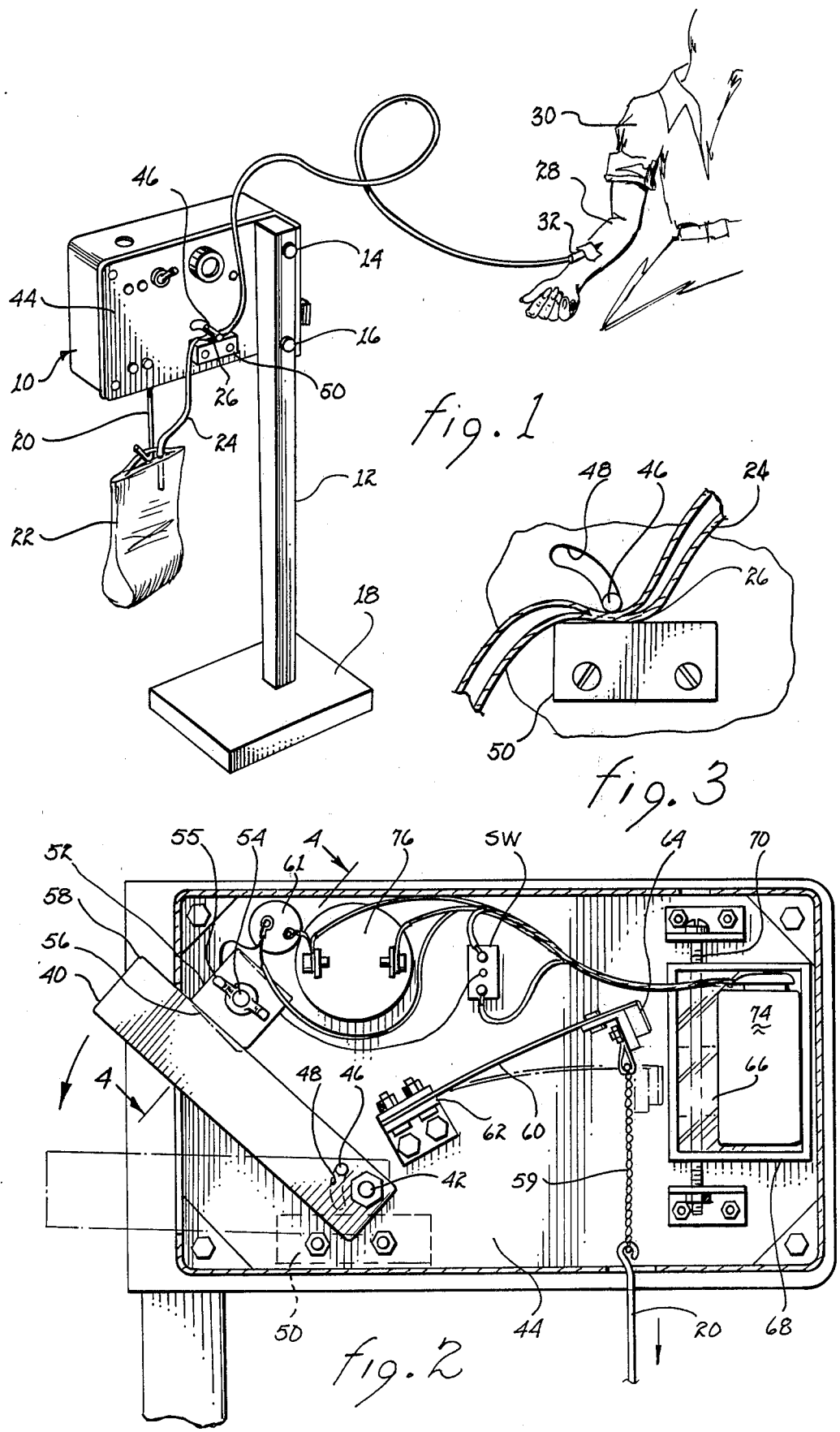

BLOOD COLLECTION BAG WEIGHING DEVICE

This is a continuation, of application, Ser. No. 81,164, filed Oct. 2, 1979 now abandoned.

The present invention relates to weighing devices for blood collection bags and, more particularly, to devices for releasing stored energy by short duration, low energy disruption of a magnetic field.

In private and public blood collection centers, whether for profit, for charity or in affiliation with a hospital, relatively crude techniques are employed to determine the degree of fill of each blood collection bag. In poorly funded blood collection centers, the degree of fill is monitored by one or more operators which results in substantial diversity in the amount of blood in the blood collection bags. Such diversity or nonuniformity may result in penalties or other strictures imposed by a monitoring federal agency for over filled blood collection bags. Where payment by the blood collection center to the blood donors is made on a per blood collection bag basis, overpayment occurs when the blood collection bags are not filled to their norm.

Static weight monitoring apparatus have been employed which provide a visual indication, such as a scale, to an operator upon fill of a blood collection bag commensurate with a norm. Thereafter, further flow is terminated by the operator. Other apparatus which actuate mechanical, electrical or electro mechanical elements on achievement of an approximated weight, have also been developed. One of the more sophisticated apparatus which employs dynamic, rather than static, weighing of the blood collection bag during fill is described in U.S. Pat. No. 4,027,735, which patent is assigned to the present assignee. The apparatus described therein continuously agitates the blood collection bag during fill to obtain good mixing with preservatives predisposed within the blood collection bag while simultaneously weighing the blood collection bag and terminating further flow thereinto on achievement of a predetermined weight.

The apparatus which relies upon the weight of the blood collection bag to generate an indication of the state of fill or for terminating further flow of blood, inherently negatively affects the weighing accuracy. Prior art apparatus which terminates the flow of blood into a filled blood collection bag in response to a signal generated by or as a result of the state of fill of the blood collection bag requires a source of electrical or mechanical power to actuate blood flow terminating equipment. This requirement limits the agility of the apparatus to locations where such electrical or mechanical power must be transported along with the apparatus to remote locations. Should the electrical or mechanical power not be available in situ or through portable motor/generator sets, the operation of the blood collection center must be monitored solely by operators which results in nonuniformity in the fill of the blood collection bags, as described above.

To achieve uniformity of fill of blood collection bags and remove a dependency upon an in situ or transportable source of substantial power, the device described hereinafter was developed. This device employs a blood collection bag weight responsive trigger to generate a very low energy electrical signal from a self-contained source of electrical power to release stored energy and perform the work required. Thereby, the device is readily fully self-contained and will accurately monitor and terminate the filling process of blood collection bags.

It is therefore a primary object of the present invention to provide a monitoring device for terminating the flow of blood into a blood collection bag on achievement of the predetermined weight of fill.

Another object of the present invention is to provide a blood collection monitoring device which employs a source of stored mechanical energy to terminate on command further flow of blood into a blood collection bag.

Yet another object of the present invention is to provide a low energy triggering mechanism for triggering the release of stored mechanical energy to terminate the flow of blood into a blood collection bag.

Still another object of the present invention is to provide a low cost, self-contained device for continuously weighing a blood collection bag during filling thereof and terminating the filling on achievement of a predetermined weight of the bag.

A further object of the present invention is to provide a low energy consumption triggering mechanism for momentarily disrupting the magnetic field of a permanent magnet, which disruption releases stored energy to perform useful work.

A yet further object of the present invention is to provide a momentarily accuated electrical circuit for momentarily disrupting the field of a permanent magnet to release a magnetically retained element.

A still further object of the present invention is to provide a circuit for disrupting the magnetic field of a permanent magnet and subsequently employ the energy thereby stored in a capacitor of the circuit to generate an indication to an operator that disruption has occurred.

These and other objects of the present invention will become apparent to those skilled in the art as the description thereof proceeds.

The present invention may be described with greater specificity and clarity with reference to the following drawings in which:

FIG. 1 illustrates the blood collection bag weighing device in operation;

FIG. 2 illustrates the various components of the weighing device;

FIG. 3 is a partial view illustrating the operation of the tubing clamp;

Figure 4:
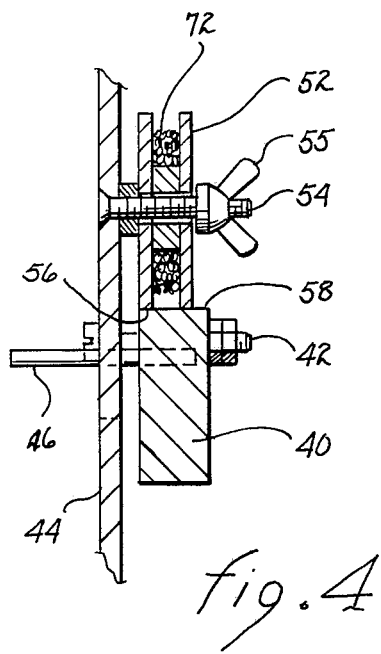
FIG. 4 is a cross-sectional view taken along lines 4—4 as shown in FIG. 2.

Referring to FIG. 1, there is shown a weighing device 10 supported upon a post 12 by means such as bolts 14 and 16. The post is anchored to and extends upwardly from a pedestal or platform 18. A hook 20 depends from weighing device 10 to suspendingly support a blood collection bag 22. Fill tube 24 extends from the interior of the blood collection bag via actuatable clamp 26 to an arm 28 of a donor 30. As is well known, the end of tubing 24 is terminated by a needle 32 inserted into the artery of the donor. To achieve a satisfactory gravity augmented flow rate from the donor to the collection bag, the collection bag should be maintained at the height slightly below that of needle 32.

The structure and operation of clamp 26 will be reviewed with joint reference to FIGS. 2, 3 and 4. The clamp includes a weighted member or bar 40 of steel or of other magnetically responsive material, and which bar is pivotally mounted upon bolt 42 extending rearwardly from face plate 44. A rod 46 extends from bar 40 through a curved slot 48 in the face plate and positionable in proximity with anvil 50 mounted to the front of the face plate. The relationship of these components is such that in the downwardly pivoted position of bar 40, (shown in dashed lines in FIG. 2) rod 46 may lie upon and be supported by anvil 50 to insure that anything disposed intermediate the anvil and the rod will be squeezed by a force equivalent to the effective moment arm of the rod times the weight of the bar. The bar is maintained in the cocked or raised position by permanent magnet 52. The magnet is loosely mounted upon bolt 54 by thumbscrew 55 to insure continuing alignment conformance between face 56 of the magnet and side 58 of bar 40 and insure maximum magnetic retention force therebetween.

When bar 40 is in the raised position, sufficient space exists intermediate rod 46 and the upper surface of anvil 50 to accommodate tubing 26 therebetween without undue squeezing of the tubing and constriction upon the flow of blood therethrough. On disengagement between magnet 52 and bar 40, the bar will pivot downwardly about bolt 42 until further downward pivotal movement is constrained by rod 46. Such constraint upon further pivotal movement is presented by tubing 26 and the underlying anvil; see FIG. 3. In the downward pivotal position of bar 40, as illustrated by the dashed lines in FIG. 2, the downward force exerted by rod 46 results in squeezing of tubing 26 and complete restriction of further blood flow therethrough. Thus, further fill of blood bag 22 (see FIG. 1) is constrained by the weight of the bar acting through rod 46.

Figure 5:
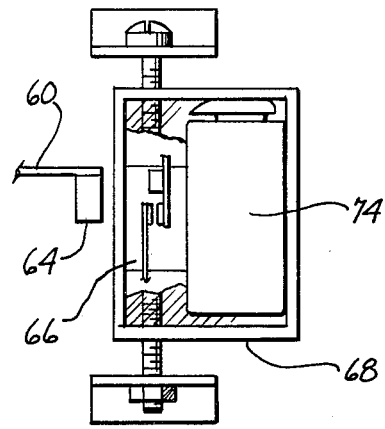
FIG. 5 is a partial cross-sectional view of the switch mechanism.

The blood collection bag weight sensing apparatus will be described with primary reference to FIGS. 2 and 5. Hook 20, supporting blood collection bag 22, is suspended by chain 59 from a leaf spring 60. One end of the leaf spring is rigidly attached to face plate 40 by bracket 62 and the other end is free to move in a vertical plane. A magnet 64 is attached in proximity to the free end of the leaf spring for cooperation with a magnetically responsive reed switch 66 disposed within housing 68.

As the blood collection bag is filling, its weight will increase commensurate with the volume of fill. The increasing weight of the blood collection bag will draw the free end of the leaf spring downwardly. By relocating housing 68 by means of lead screw 70 the reed switch can be positioned in operative proximity to the location of magnet 64 when the free end of the leaf spring is vertically displaced commensurate with the predetermined filled weight of the blood collection bag. Thus, the reed switch will be actuated by the magnet when the blood collection bag is filled to the predetermined weight. The lead screw may also be used to counteract long term drift of the mechanical components, i.e., for periodic calibration. As will be described in further detail below, this actuation of the reed switch is employed to generate a signal to terminate further flow of blood into the blood collection bag.

A coil of wire 72 is disposed in proximity to permanent magnet 52 in such a manner as to cause cancellation or at least disruption of the magnetic field produced by the permanent magnet on electrical energization of the coil. In the embodiment illustrated, the coil is disposed intermediate the two pole pieces of the permanent magnet assembly. Disruption of the magnetic field of magnet 52 will produce a reduced magnetic retention capability of the magnet. Empirically or by engineering analysis the field strength of the permanent magnet is selected to be sufficient to retain bar 40 thereagainst with a margin of safety. A disruption of the magnetic field sufficient to reduce the magnetic force to a value insufficient to retain the bar will cause release of the bar. Assuming that the magnetic field disruption produced by the coil is enough to reduce the magnetic retention force below a minimum, bar 40 will be released. As soon as release, that is, physical separation between the magnet and bar, is effected, an air gap will develop. The air gap substantially impairs the retention capability of the magnet. By experimentation, it has been learned that a disruption of the magnetic field for approximately one millisecond will result in the development due to the force of gravity of an air gap of approximately five microns. This air gap, even though very minute, combined with the momentum of the falling bar 40, prevents recapture of the bar by the magnet and the bar will continue to drop and pivot about bolt 42. The resulting repositioning of the bar will bring rod 46 to bear against and squeeze tubing 26, as described above.

Figure 6:
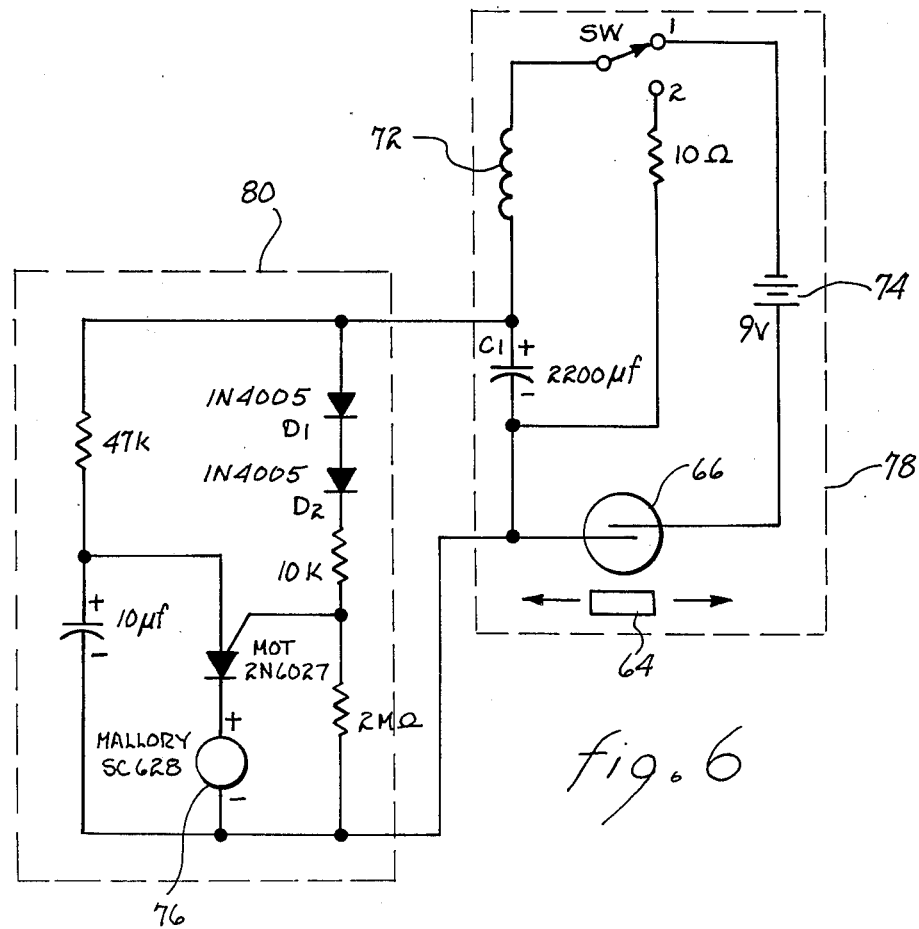
FIG. 6 is a schematic diagram.

Referring to FIG. 6, there is illustrated within block 78 a circuit for generating a short duration low energy pulse for disrupting the magnetic field of magnet 52. When magnet 64 is brought into proximity with microswitch 66, the microswitch will be actuated and close. Closing of the microswitch will complete the circuit and battery 74 will charge capacitor $C_1$ through switch SW and through coil 80; it is assumed that switch SW is spring loaded to state 1, otherwise it will have to be switched to state 1. The momentary current flow through the coil to charge the capacitor (a duration of approximately one millisecond for the component values illustrated and with a coil resistance of approximately 0.5 ohm) is sufficient to disrupt the magnetic field attendant magnet 52. Consequently, bar 40 will be released, as described above. After capacitor $C_1$ has become charged, no further flow of power from battery 74 will occur, except for minor and essentially inconsequential leakage losses. To reset the circuit, the switch may be switched to state 2 which would discharge capacitor $C_1$ through the 10 ohm resistor.

As the charged capacitor represents a source of useable power, relaxation oscillator illustrated in block 80, may be employed to utilize this otherwise wasted power to provide an audible indication to an operator that flow to the blood collection bag has been terminated. As is well known, the relaxation oscillator generates a series of pulses, which pulses are employed to energize a beeper 76. This beeper will emit an audible tone periodically for a limited duration until the charge upon capacitor $C_1$ has been consumed. After the operator's attention has been drawn, further, emission of the audible tone may be terminated by the operator by switching switch SW to state 2 and thereby discharging capacitor $C_1$. It may be noted that no power is drawn from battery 74 to energize the relaxation oscillator or beeper 76.

By experimentation, it has been learned that conventional and readily commercially available 9 volt batteries (generally referred to as transistor radio batteries) may be employed. Such a battery is small, lightweight, inexpensive and is readily mountable permanently within housing 68, as illustrated in FIG. 5. The energy capacity of a 9 volt battery of this type is approximately 8,000 joules. The amount of energy consumed per change of capacitor $C_1$ (or per pulse transmitted to coil 72) may be calculated by the formula $\frac{1}{2}CV^2$. For the circuit values enumerated in FIG. 6, approximately 0.08 joules per charge are consumed. Considering the battery energy capacity, a conventional inexpensive 9 volt battery will have sufficient energy for approximately 100,000 charges of the capacitor. Normal use of a blood collection bag weighing device in a blood collection center suggests approximately 4,000 filled blood collection bags per year. Thus, replacement of battery 74 may be required every 25 years and replacement is therefore primarily a function of the shelf life of the battery. The added expense of rechargeable batteries is not justified. Accordingly, the operating expenses are extremely low. It may be noted that there exists no need for any other external or internal sources of electrical or mechanical power.

It is to be noted that other means, such as a solenoid, could be used to import an impact to the bar by the armature on energization to cause an air gap to develop between the permanent magnet and the magnetically retained bar. The energy consumption of the solenoid would be relatively minor, though probably more than that of charging capacitor $C_1$.

While the above description of the present invention has been primarily couched within the context of a weighing device for blood collection bags, the essential features of the present invention may have use in many totally unrelated fields. That is, the gist of the present invention is that of releasing stored mechanical potential energy maintained by a permanent magnet through generation of a short duration low energy magnetic field to disrupt the magnetic field of the permanent magnet. Various applications of this principle which come to mind in areas unrelated to the present invention include the following:

(1) the use of a permanent magnet in place of an electromagnet for transporting ferrous materials in junkyards, material handling locations, etc; the only requirement for electrical power would exist at such time as the retained material was to be released. The difference in quantity of electrical power consumption between the prior art devices and a device incorporating the present invention is very substantial;

(2) a magnet could be employed to maintain the firing pin of a firearm in the cocked position. The trigger would not have to perform a mechanical release function but could be employed simply to close a circuit to disrupt the magnetic field of the magnet and permit release of the firing pin in response to a cocked spring acting upon the firing pin. By avoiding the mechanical impediments to triggers, flinching, anticipation and other accuracy robbing reflexes are avoided.

(3) traps, fish hooks and similar devices presently relying primarily upon mechanical triggering means requiring certain forces could be adapted to incorporate the features of the present invention and thereby avoid the mechanical impediments attendant the respective triggering mechanisms;

(4) latching relays, such as bistable relays having a permanent magnet and a field disruptive coil corresponding with each state and permitting switching from one state to another by selective actuation of one of the coils;

(5) any device wherein it is advantageous to employ extremely low triggering forces to initiate high actuation forces;

(6) any device wherein it is preferable to have a triggering force totally unrelated in magnitude to the value of the force to be released; and (7) any device requiring a high resolution low power trigger or initiation signal to release or actuate a substantial source of potential energy.

In addition to the form of stored energy already discussed, namely mechanical potential energy, there exist other forms of stored energy that may be released to perform useful work by the momentary disruption of the magnetic field of a permanent magnet. For example, mechanical kinetic energy may be stored in the form of the rotating flywheel, the axel of which is supported by a permanent magnet against some bias force, such as gravity. By momentarily disrupting the field of the permanent magnet, the flywheel could be released to move to a new position as a result of the applied bias force. In this new position the fly wheel could rest against a driven wheel and cause the driven wheel to rotate and perform some useful work. As a second example, the stored energy could be electrodynamic energy embodied by charged particles, such as electrons, circulating in a cyclotron in which the magnetic field is produced by permanent magnets. The field of the permanent magnets may be momentarily disrupted to allow the charged particles to escape the circular path to perform some useful work.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A blood collection bag weighing device for filling a blood collection bag with a predetermined weight of blood flowing from a tube extending from the vascular system of a donor, said device comprising in combination:

(a) means for clamping the tubing, said clamping means including a member for embodying stored potential energy when positioned in a retained state and for clamping the tube when positioned in a clamping state, said member including a planar surface and means for exerting a first magnitude of force against retention in the retained state and a second magnitude of force for clamping the tubing in the clamped state, which second magnitude of force is substantially greater than the first magnitude of force;

(b) a permanent magnet for overcoming the first magnitude of force to magnetically capture and retain said member in the retained state, said magnet including a straight edge and movable mounting means for accommodating realignment of said magnet to position said straight edge of said magnet in aligned contacting relationship with said planar surface of said member and maximize the magnetic coupling therebetween;

(c) means for momentarily disrupting the magnetic field of said magnet to a value insufficient to overcome the first magnitude of force and independent of the magnitude of the second magnitude of force and permit repositioning of said member from the retained state to the clamping state in response to said exerting means;

(d) means for sensing achievement of the predetermined weight by the blood collection bag during the filling of the blood collection bag; and (e) means for generating an electrical signal in response to said sensing means to energize said disrupting means;

whereby, the energy level of said magnet and of said generated electrical signal may be unrelated to the level of energy of the second magnitude of force to clamp the tubing.

2. The device as set forth in claim 1 wherein said member comprises a pivotally mounted bar pivotable to the clamping state in response to the second magnitude of force and independent of the first magnitude of force.

3. The device as set forth in claim 2 wherein said device includes an anvil for supporting the tubing and said member includes a rod for squeezing the tubing against said anvil on positioning of said member in the clamped state to preclude further flow through the tubing.

4. The device as set forth in claim 3 wherein said magnet comprises a pair of spaced apart plates.

5. The device as set forth in claim 4 wherein said disrupting means comprises an electrical coil disposed intermediate said pair of plates.

6. The device as set forth in claim 1 wherein said generating means includes a capacitor and a 9 volt battery for charging said capacitor.

7. The device as set forth in claim 6 wherein said disrupting means comprises a coil disposed in proximity to said magnet for generating a magnetic field to at least partially cancel the magnetic field attendant said magnet in response to discharge of said capacitor through said coil.

8. The device as set forth in claim 7 wherein said disrupting means further comprises a normally open switch closed upon fill of the blood bag to a predetermined weight for discharging said capacitor.

* * * * *